(12) United States Patent
Boiten

(10) Patent No.: US 10,251,761 B2
(45) Date of Patent: Apr. 9, 2019

(54) PROSTHETIC KNEE JOINT

(71) Applicant: OTTO BOCK HEALTHCARE GMBH, Duderstadt (DE)

(72) Inventor: Herman Boiten, Gottingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 15/109,365

(22) PCT Filed: Dec. 31, 2014

(86) PCT No.: PCT/EP2014/003483
§ 371 (c)(1),
(2) Date: Jun. 30, 2016

(87) PCT Pub. No.: WO2015/101417
PCT Pub. Date: Jul. 9, 2015

(65) Prior Publication Data
US 2016/0324665 A1    Nov. 10, 2016

(30) Foreign Application Priority Data
Jan. 3, 2014  (DE) .......................... 10 2014 000 020

(51) Int. Cl.
*A61F 2/64*    (2006.01)
*A61F 2/50*    (2006.01)

(52) U.S. Cl.
CPC ...... *A61F 2/644* (2013.01); *A61F 2002/5003* (2013.01); *A61F 2002/5007* (2013.01);
(Continued)

(58) Field of Classification Search
CPC ............. A61F 2/64; A61F 2/644; A61F 2/607
(Continued)

(56) References Cited

U.S. PATENT DOCUMENTS 5,181,931 A    1/1993  van de Veen
5,314,498 A    5/1994  Gramnas
(Continued)

FOREIGN PATENT DOCUMENTS

CN        1123133 A       5/1996
CN        103384506 A     11/2013
(Continued)

OTHER PUBLICATIONS

PCT International Search Report for PCT International Patent Application No. PCT/EP2014/003483, dated Mar. 25, 2015.
(Continued)

*Primary Examiner* — Bruce E Snow
(74) *Attorney, Agent, or Firm* — Holland & Hart LLP

(57) ABSTRACT

A prosthetic knee joint includes an upper part, a lower part which is arranged pivotably to the upper part, a fastening device arranged on the upper part for a proximal prosthetic element, a fastening device arranged on the lower part for a distal prosthetic element, a four-limbed joint system with four linkages articulatedly fastened to each other, which are each pivotable to each other around a pivot axis, wherein the upper part (10) is arranged on the joint system. The joint system may be mounted pivotably on the lower part from a starting position counter to a spring force during a stance phase flexion, and the action line of the spring force may be aligned such that a moment acting against an inflexion of the joint system is present.

18 Claims, 3 Drawing Sheets

(52) U.S. Cl.
CPC ............. *A61F 2002/5009* (2013.01); *A61F 2002/5087* (2013.01)

(58) Field of Classification Search
USPC ...................................................... 623/43–44
See application file for complete search history.

(56) References Cited

U.S. PATENT DOCUMENTS

| | | | |
|---|---|---|---|
| 5,545,232 A | 8/1996 | van de Veen | |
| 5,645,590 A | 7/1997 | van de Veen | |
| 5,728,173 A | 3/1998 | Chen | |
| 6,086,616 A | 7/2000 | Okuda et al. | |
| 6,706,074 B1 | 3/2004 | Chen | |
| 6,808,540 B1 | 10/2004 | Gramnas | |
| 7,001,434 B2* | 2/2006 | Van De Veen | A61F 2/644 623/39 |
| 7,044,983 B1 | 5/2006 | Cheng | |
| 7,087,091 B1* | 8/2006 | Chen | A61F 2/644 623/44 |
| 9,775,715 B2 | 10/2017 | Boiten | |
| 2005/0038528 A1 | 2/2005 | McKelvey et al. | |
| 2012/0310372 A1 | 12/2012 | Omarsson et al. | |
| 2013/0085580 A1 | 4/2013 | Wu et al. | |
| 2013/0103167 A1 | 4/2013 | Chen et al. | |
| 2013/0173021 A1* | 7/2013 | Chen | A61F 2/644 623/46 |

FOREIGN PATENT DOCUMENTS

| | | |
|---|---|---|
| DE | 102009053128 A1 | 7/2010 |
| DE | 202011108817 U1 | 3/2012 |
| DE | 102010050318 A1 | 5/2012 |
| DE | 202012010124 U1 | 3/2013 |
| EP | 0713689 A1 | 5/1996 |
| GB | 2467201 A | 7/2010 |
| RU | 2294715 C2 | 7/2005 |
| RU | 47732 U1 | 9/2005 |
| RU | 74291 U1 | 6/2008 |

OTHER PUBLICATIONS

EC Declaration of Conformity Certificate, valid from Jun. 10, 2005, last updated Jul. 16, 2018 (29 pp.).
Prosthetics Catalog, Ossur Total Knee 1900, Apr. 2007 (15 pp.).
Prosthetics Product Catalog, Ossur Total Knee 1900, 2010 (12 pp.).
Instructions for Use, Ossur Total Knee 2000, 2010 (96 pp.).
Instructions for Use, Ossur Total Knee 1900, 2011 (92 pp.).
Instructions for Use, Ossur Total Knee 2100, 2011 (76 pp.).
Instructions for Use, Ossur Total Knee Junior, 2011 (75 pp.).
Lindner, Ann-Kathrin, "Beeinflussung der Kinematik und Symmetrie des Gangbildes von Oberschenkelamputierten durch Veränderung des distalen Prothesengewichts," Dissertation, Westfälischen Wilhelms-Universitat Münster, Nov. 15, 2011 (190 pp.).
"Die acht Gangphasen des Menschen," Streifeneder, available at least as early as Jan. 3, 2014 (2 pp.).

* cited by examiner

PROSTHETIC KNEE JOINT

TECHNICAL FIELD

The invention relates to a prosthetic knee joint comprising an upper part, a lower part, which is arranged pivotably with respect to the upper part, a fastening device arranged on the upper part and provided for a proximal prosthetic element, a fastening device arranged on the lower part and provided for a distal prosthetic element, and a four-member joint system with four joint members which are fastened to one another in an articulated manner and are pivotable with respect to one another about a respective pivot axis, wherein the upper part is arranged on the joint system.

BACKGROUND

EP 0 713 689 A1 discloses a prosthetic knee joint with an upper part, and with a lower part fastened to the latter in an articulated manner. The coupling of upper part and lower part is effected via a multi-element, kinematic joint chain with at least four joint members, in which the members respectively connected to one another have a common rotation axis. The rotation axes extend substantially parallel to one another; in the starting position of the multi-element joint system, one joint member can execute two movements with respect to the other members connected to it, wherein at least one movement, following its initiation, blocks the other possible movement at least for the most part. With such a device, it is possible to permit a stance phase flexion without completely blocking a buckling of the prosthetic knee joint.

The problems of prosthetic knee joints with length-adjustable joint members are the relatively complex construction and the possibility that a geometric barrier of the joint system arises when giving-way during the stance phase flexion. A geometric barrier of a prosthetic knee joint is described, for example, in U.S. Pat. No. 5,314,498, in which the aim is to simulate the function of a natural knee joint by means of a polycentric construction and to permit automatic geometric locking in a simple manner.

SUMMARY

The object of the present invention is to make available a prosthetic knee joint which has a simple arrangement of the components and which ensures that a buckling of the prosthetic knee joint is in principle possible even during the stance phase flexion.

According to the invention, this object is achieved by a prosthetic knee joint having the features of the main claim. Advantageous embodiments and developments of the invention are disclosed in the dependent claims, the description and the figures.

In the prosthetic knee joint according to the invention comprising an upper part, a lower part which is fastened on the upper part in a manner pivotable thereto, a fastening device arranged on the upper part and provided for a proximal prosthetic element, a fastening device arranged on the lower part and provided for a distal prosthetic knee joint, and a four-member joint system with four joint members, which are fastened to one another in an articulated manner and are pivotable with respect to one another about a respective pivot axis, wherein the upper part is arranged on the joint system, provision is made that the joint system is mounted on the lower part so as to be pivotable from a starting position counter to a spring force during the stance phase flexion, and the action line of the spring force is oriented such that a moment acting against the buckling of the joint system is present, in particular also in a joint system pivoted with respect to the starting position or in an extended joint system, that bears against the extension stop and in its entirety is displaced relative to the lower part on account of the forces acting in the stance phase flexion. By means of the orientation of the action line of the spring force by suitable arrangement and orientation of the joint points, for example of a spring element designed as a length-adjustable joint member of a multi-link system, it is possible that, during a stance phase flexion, a securing moment is applied to the joint system, without this changing the geometric structure and the assignment of the joint members in the joint system. The joint system is pivoted in its entirety, without the prosthetic knee joint buckling as a result of a displacement of the joint members of the joint system with respect to one another. Despite an additional moment acting counter to buckling of the joint system in the stance phase flexion, it is thus possible in principle that, upon application of a sufficiently high flexion moment, e.g. the hip flexion moment, the prosthetic knee joint buckles, with the result that a geometric lock does not occur. This is achieved in particular by the fact that the joint members of the joint system are designed to be unmodifiable in length and are arranged as a system, unmodified in their position with respect to one another, pivotably on the lower part.

In a development of the invention, provision is made that the moment acting counter to buckling of the joint system is increased as the angle of pivoting of the joint system with respect to the lower part increases in stance phase flexion. In the event of an increasing angle of pivoting, it is not only the spring force that increases, but also the effective lever arm, as a result of which there is a double increase in moment, such that at a maximum stance phase flexion there is a maximally effective moment against buckling of the prosthetic knee joint by a change of the positions of the joint members with respect to one another. Although the upper part and the lower part are displaced relative to each other by the giving-way in a direction counter to the spring force, this is not buckling of the prosthetic knee joint caused by a change of orientation of the joint members of the joint system with respect to one another.

In a development of the invention, provision is made that the joint system is mounted on a multi-link system, of which the pivot axes do not coincide with the pivot axes of the joint system. This leads to a staggering of the bearing points of the respective systems, i.e. of the joint system and of the multi-link system, such that no bearing points lie near each other and, as a result, the bearing widths can be dimensioned to be sufficiently stable.

The joint system can have a mechanical extension stop against which the joint system bears in the extended position. A stance phase flexion will generally occur when a prosthetic knee joint is extended, such that the joint system bears on the mechanical extension stop in the event of what is called heel strike. For example, this can happen by means of one of the joint members bearing on the mechanical extension stop and thereby preventing further displacement of the joint member in the extension direction and thus preventing a corresponding relative displacement of the joint members with respect to one another.

The joint system can have a distal joint member which has a further anterior pivot axis which is arranged distally in relation to the anterior pivot axis of the joint system and about which the joint system is mounted pivotably on the lower part. The distal joint member thus has two functions, firstly the connection of two joint members of the joint system, namely the anterior joint member and the posterior joint member, and in addition the formation of a pivot axis or a bearing point for a pivot axis, in order to connect the joint system to the lower part and thus make available a multi-link system for the pivotable bearing of the joint system on the lower part.

The joint system can additionally have a posterior joint member which has a proximal pivot axis and a distal pivot axis, wherein the posterior joint member is continued beyond the distal pivot axis and, in the continuation, has a proximal pivot axis for a spring element which is part of the multi-link system. The posterior joint member thus likewise provides a bearing point of the multi-link system, specifically in the area of the distal continuation beyond the distal, posterior pivot axis of the joint system.

The spring element can have a distal bearing point, which can be arranged on the lower part, wherein the connecting line between the distal bearing point of the spring element and the proximal pivot axis of the multi-link system extends anteriorly with respect to the distal pivot axis of the posterior joint member of the joint system. This ensures that, upon application of a force to the spring element in the stance phase flexion, the geometric assignment and the action line of the force introduction points generate a moment which counteracts a buckling of the prosthetic knee joint, i.e. a pivoting of the joint system and thus a displacement and buckling of the upper part relative to the lower part.

The spring element, which supports the joint system in relation to the lower part and permits giving-way in the stance phase, does not simply have to be produced as a pure spring element, but also can be designed as a spring damper element or spring damper system, in order to make available a restoring force counter to the giving-way of the joint system. In an embodiment of the spring element with a damper component, the damping can be made available via a fluid damper or an elastomer damper. The elastomer damper can have an elastomer element or be composed of an elastomer element which is formed from a plastics composite. The elastomer element can be designed as a tube or can at least have a tube, it being possible for several elastomer elements to be connected in series.

A spring element can be arranged on a distal joint member of the joint system and is supported on the proximal joint member of the joint system. By way of this spring element, it is possible to influence the behavior of the prosthetic knee joint during normal buckling, i.e. during the swing phase, or upon buckling of the prosthetic knee joint in the region of the terminal stance phase. Analogously to the spring element between the joint system and the lower part, the spring element of the joint system can be designed not only as a pure spring element but also as a spring damper element or spring damper system which provides a restoring force with which the joint system is moved to a starting position, in particular the fully extended position, when no other forces act on the prosthetic knee joint. In a design of the spring element with a damper component, the damping can be provided by a fluid damper or an elastomer damper. The elastomer damper can have an elastomer element or can be composed of an elastomer element formed from a plastics composite. The elastomer element can be designed as a tube or can at least have a tube, it being possible for a plurality of elastomer elements to be connected in series.

The joint system is advantageously supported on the lower part via a spring element, wherein the fastening points of the spring element do not coincide with the pivot axes of the joint system, as a result of which there is a staggering of the bearing points. Thus, no bearing point of the joint system coincides with a bearing point of the multi-link system, such that all of the bearing points or connecting points of the joint members, both of the joint system and also of the multi-link system, can be designed separately and can be dimensioned with sufficient strength. The joint members of the joint system are preferably unmodifiable in length, whereas at least one of the joint members of the multi-link system is modifiable in length, such that a change of the geometry of the multi-link system takes place not only through a rotation of two joint members fastened to each other, but also through a change of length of the joint members and a change of the distance between the bearing points of a joint member.

If a spring element is provided, it can be designed as a compressible elastomer element, as a result of which it is possible, with a low overall height and a small installation space, to apply high spring forces, in addition to which such an elastomer element is maintenance-free, quiet and very light. The spring element can be arranged both in the joint system and also in the multi-link system.

The spring element can be designed to be adjustable in terms of the restoring force in order to permit an adjustment of the prosthesis to the respective patient. The adjustability can be provided for one or both of the spring elements. The respective spring element can be pre-tensioned and, via the pre-compression, can influence the resistance against buckling or the resistance against giving-way of the joint system. In the case of the spring element between the joint system and the lower part as part of the multi-link system, the degree of pre-compression, which is adjustable or modifiable, can permit an adaptation to the patient's own weight or to the intended load.

BRIEF DESCRIPTION OF THE DRAWINGS

An illustrative embodiment of the invention is explained in more detail below with reference to the attached figures, in which.

DETAILED DESCRIPTION

Figure 1:
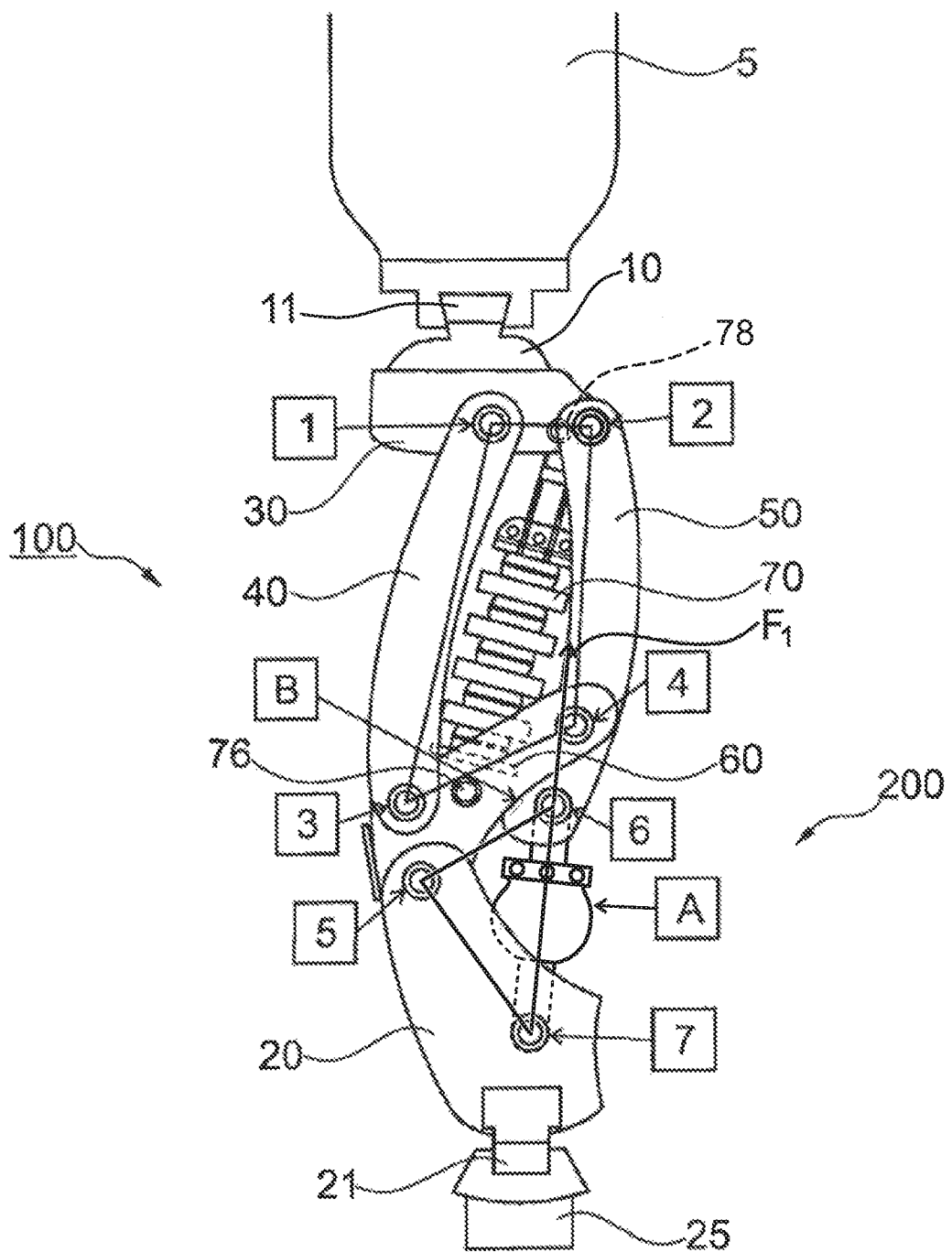
FIG. 1 shows a schematic view of a prosthetic knee joint in a fully extended position.

The illustrative embodiment of a prosthetic knee joint shown in FIG. 1 has an upper part 10, on which a fastening device 11 is provided in the form of an attachment pylon for a distal prosthetic component 5, for example for fastening the prosthetic knee joint on a thigh tube or on a thigh socket. The fastening device 11 can be screwed into the upper part 10 or can be formed in one piece with the latter. A first joint member 30 (also referred to as a proximal joint member 30) of a four-member joint system 100 can be arranged or formed on the upper part 10. The proximal, substantially horizontally oriented first joint member 30 has an anterior pivot axis 1 and a posterior pivot axis 2. An anterior joint member 40 is mounted pivotably on the anterior pivot axis 1, and a posterior joint member 50 is mounted pivotably on the posterior pivot axis 2. Thus, the proximal end of the anterior joint member 40 is pivotably connected to the upper part 10 or the proximal joint member 30 via the pivot axis 1, and the proximal end of the posterior joint member 50 is pivotably connected to the upper part 10 or the proximal joint member 30 via the pivot axis 2.

The distal end of the anterior joint member 40 is mounted pivotably on a distal joint member 60 at a pivot axis 3. The pivot axis 3 is arranged on the anterior end of the distal joint member 60. A fourth pivot axis 4 is arranged on the posterior end of the distal joint member 60, where the proximal bearing point of the posterior joint member 50 of the four-member joint system 100 is mounted. The joint system 100 is thus formed by the four pivot axes 1, 2, 3 and 4 of the four joint members 30, 40, 50 and 60. The joint members 30, 40, 50, 60 are of a rigid configuration, such that the distance between the pivot axes 1, 2, 3, 4 within the joint members 30, 40, 50, 60 remains unchangeable; by means of a rotation of the joint members with respect to one another, it is possible for the upper part 10 to be buckled for the buckling of the prosthetic knee joint, for example during a swing phase. The buckling can amount to almost 180°. The upper part 10 is buckled relative to a lower part 20 by the displacement of the joint members 30, 40, 50, 60 of the four-member joint system 100. Analogously to the upper part 10, the lower part 20 has a fastening device 21, which serves to fasten a distal prosthetic element 25, for example a prosthetic foot or, as shown, a below-knee tube.

The distal joint member 60 has, in addition to the distal pivot axis 3, a further pivot axis 5, which is spaced apart distally from the pivot axis 3, such that the whole joint system 100 can be pivoted about the pivot axis 5 relative to the lower part 20, even when there is no buckling of the upper part 10 by displacement of the joint members 30, 40, 50, 60 of the joint system 100 with respect to one another. For this purpose, provision is made that, in the distal direction from the distal, posterior pivot axis 4, a continuation of the posterior joint member 50 is formed on which a distal, posterior pivot axis 6 is arranged, where a spring element A is fastened which is supported on the lower part 20 at a lower pivot axis 7. By means of the pivot axes 5, 6, 7, a multi-link system is thus formed which, by the spring element A, forms the connection between joint axes 5, 7 arranged on the lower part 20 and the connection between the proximal pivot axis 5 on the lower part 20 and the distal continuation of the posterior joint member 50 of the pivot axis 6 there. The length of the posterior joint member 50, lying between the pivot axes 6 and 7, of the multi-link system 200 is modifiable.

The spring element A is preferably designed as an elastomer element and allows the joint system 100 to be held in a starting position counter to a spring force. The prosthetic knee joint is shown in this starting position, in which both the spring element A presses the joint system 100 into its starting position and in which the joint system 100 is displaced to the maximum extent in the anterior direction.

In the starting position shown, the prosthetic knee joint is located in a position of maximum extension;

buckling is afforded neither by a compression of the spring element A nor by a displacement of the joint members 30, 40, 50, 60 with respect to one another. The prosthetic knee joint is extended to the maximum extent and bears on an extension stop B which, in the illustrative embodiment shown, is formed by a projection on the distal continuation of the posterior joint member 50, which projection bears on the underside of the distal joint member 60. In principle, it is also possible for the extension stop B to be differently positioned.

A further spring element 70 composed of compressible elastomer elements is arranged inside the joint system 100, which spring element 70 is mounted at the proximal end on the upper part 10 and at the distal end on the distal joint member 60. The distal bearing point 76 is located on the distal joint member 60 between the pivot axes 3 and 4. The proximal end of the spring element 70 is arranged between the proximal pivot axes 1, 2 at a proximal bearing point 78. In the illustrative embodiment shown, the fastening points of the spring element do not coincide with one of the pivot axes 1, 2, 3, 4; it is also possible in principle that one or both bearing points of the spring element 70 coincide with one or two of the pivot axes, respectively. By way of the spring element 70, it is possible to influence the buckling of the prosthetic knee joint during the swing phase or the terminal stance phase.

The operating mode of the prosthetic knee joint is such that, e.g. at the end of the swing phase, when there is a maximally extended prosthetic knee joint, the so-called heel strike takes place, in which the heel strikes the ground with the prosthetic knee joint extended. In order to absorb this heel strike, the upper part of the prosthetic knee joint with the four-member joint system 100 in the fully extended position, in which the extension stop B bears on the distal joint member 60, pivots about the pivot axis 5 and compresses the spring element A. A pivoting about the anterior pivot axis 5 of the multi-link system 200 results in only a slight displacement of the upper part 10 with respect to the lower part 20, a flexion angle of 5° is common. Already in the starting position, as is shown in FIG. 1, the force action line F, i.e. the connecting line between the bearing points 6, 7 of the spring element A, lies to the front or anterior of the distal, posterior pivot axis 4 of the four-member joint system 100, such that, upon a pivoting movement about the pivot axis 5, a force is exerted which presses the posterior joint member 50 against the distal joint member 60. In this way, a moment arises about the distal, posterior pivot axis, such that an increase of the effective moment takes place counter to a buckling of the joint system 100. As the stance phase flexion increases, i.e. with an increasing angle of pivoting about the pivot axis 5 of the multi-link system 200, the action line F of the spring force migrates in the anterior direction, as a result of which the lever about the distal, posterior pivot axis 4 increases, such that an increasing moment arises as the angle of pivoting of the joint system 100 about the pivot axis 5 increases. This increases the safety of the prosthetic knee joint against unintentional buckling by a relative movement of the joint members 30, 40, 50, 60 with respect to one another, by the pivoting about the pivot axis 1, 2, 3, 4. However, this increased safety as the stance phase flexion increases, in particular when a load is placed on the heel, does not lead to a geometric locking of the prosthetic knee joint; instead, the latter can be further buckled, by application of a hip flexion moment by changing the geometry of the joint system 100, such that it is possible to effectively prevent stumbling over an extended leg.

The prosthetic knee joint according to the invention avoids the bearing points of the individual components coinciding, such that a stable and simple construction of the prosthetic knee joint can be achieved. By virtue of the anterior course of the force action line F of the multi-link system, it is possible to provide increased safety during the stance phase flexion, in particular during the heel strike. Buckling by application of a hip flexion moment, which also takes place at the end of the stance phase for example, is readily possible.

As upper attachment means, a prosthetic socket 5 for receiving an amputation stump is indicated as proximal prosthetic element on the fastening device 11 of the upper part 10, and, as distal prosthetic element 25, a below-knee tube is arranged on the lower part 20 at the distal fastening device 21.

Figure 2:
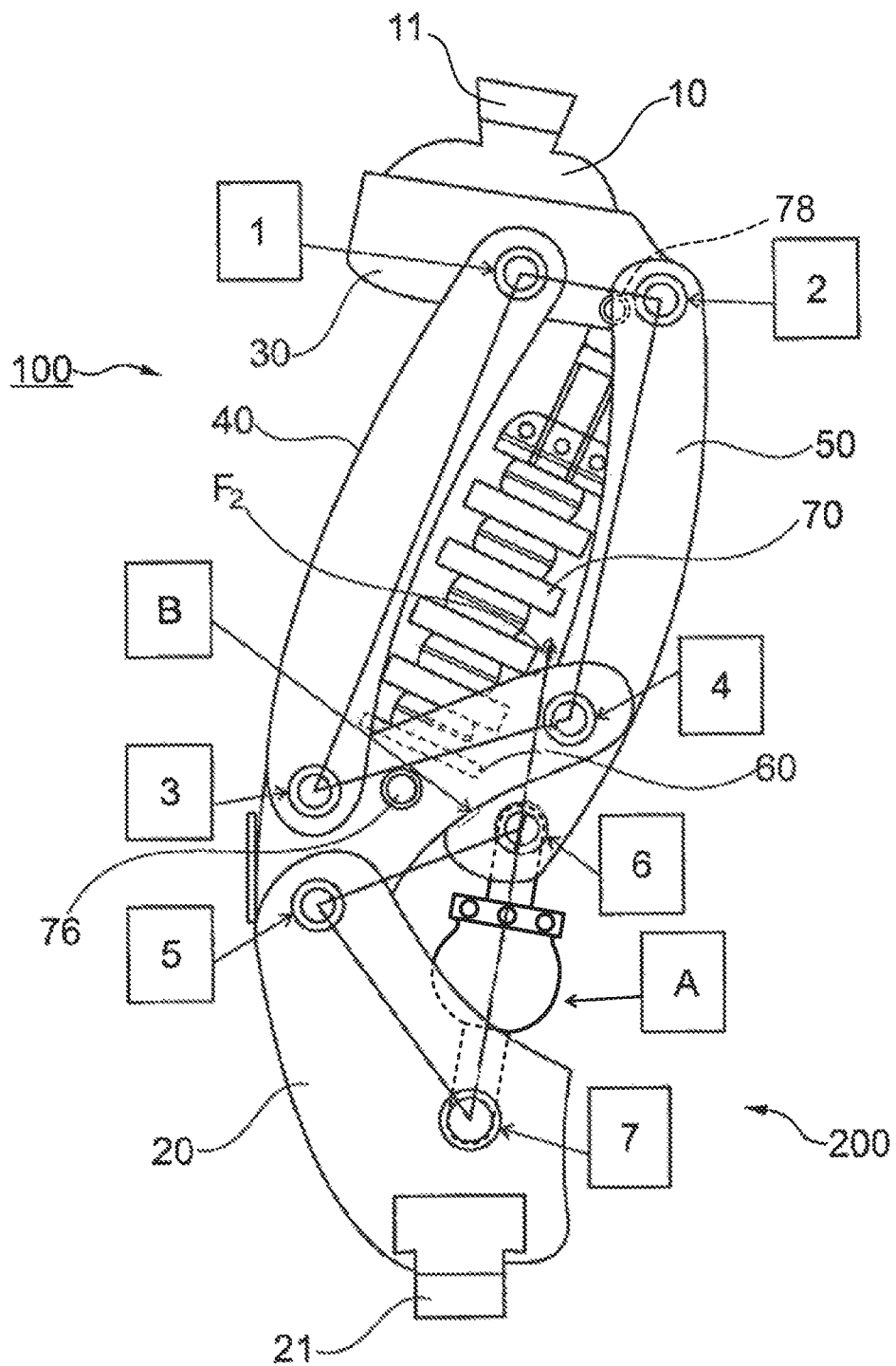
FIG. 2 shows a prosthetic knee joint with a joint system displaced relative to the lower part.

In FIG. 2, the prosthetic knee joint depicted in FIG. 1 is shown in a state in which the joint system 100, itself unmodified, is pivoted about the pivot axis 5 arranged distally in relation to the anterior, distal pivot axis 3 on the distal joint member 60. The joint system 100 with the pivot axes 1, 2, 3, 4, and with the joint members 30, 40, 50, 60 unmodified in relation to one another compared to FIG. 1, was pivoted clockwise about the pivot axis 5. The pivoting took place as a result of a change of length of the spring element A of the multi-link system 200, for example on account of the heel strike, or while standing with a load applied to the heel. The currently effective action line F2, which represents the continuation of the connecting line between the distal and proximal posterior pivot axes 6 and 7 of the multi-link system 200, is shown in FIG. 2. It will be seen in FIG. 2 that the effective action line F2, compared to the original action line F1 shown in FIG. 1, is shifted in the anterior direction with respect to the posterior, distal pivot axis 4 of the joint system 100. In this way, the lever arm about the pivot axis 4 increases, likewise the spring force as such, as a result of which a moment arises which counteracts a buckling of the prosthetic knee joint by a change of assignment of the joint members 30, 40, 50, 60 of the joint system 100. The greater the shift of the joint system 100 about the pivot axis 5 in the clockwise direction, the greater the spring force acting on the joint system 100 via the distal continuation of the proximal joint member 50, and, due to the geometric assignment, the greater the effective lever arm of the action line F of the spring force about the posterior, distal pivot axis 4, and the greater the moment acting against buckling of the joint system.

Figure 3:
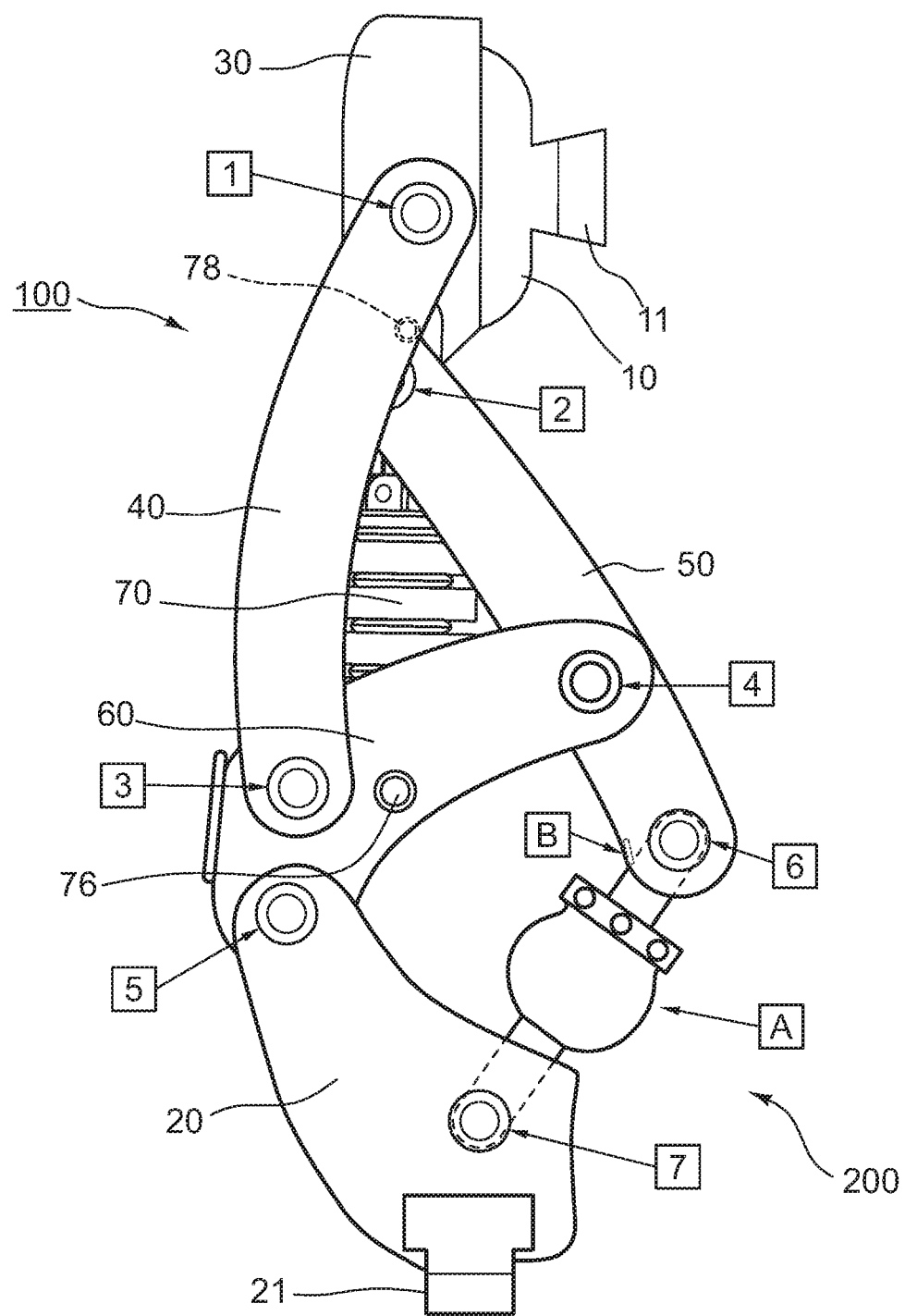
FIG. 3 shows a prosthetic knee joint at a highly flexed angle.

FIG. 3 shows the prosthetic knee joint in a highly flexed or bent arrangement in which the spring element 70 is further compressed.

The invention claimed is:

1. A prosthetic knee joint comprising:
    an upper four bar linkage system comprising a mechanical extension stop, and proximal, distal, anterior and posterior joint members pivotally connected to each other;
    a lower part having a proximal end portion pivotally connected to a distal end of the distal joint member, and a distal end portion;
    a proximal fastening device arranged at a proximal end of the upper four bar linkage system and provided for connection to a proximal prosthetic element;
    a distal fastening device arranged on the distal end portion of the lower part and provided for connection to a distal prosthetic element;
    a spring element having a distal end pivotally connected to the lower part at a location between the distal and proximal end portions of the lower part, and a proximal end pivotally connected to a distal end portion of the posterior joint member, the spring element being compressible to provide a spring force, an action line of the spring force extending in a length direction of the spring element;
    wherein the four bar linkage system is pivotable relative to the lower part from a starting position to a rotated position counter to the spring force during a stance phase flexion, and the action line of the spring force is oriented to provide a moment force on the extension stop to fix all of the joint members relative to each other and counteract a flexion buckling of the upper four bar linkage system during stance phase flexion.

2. The prosthetic knee joint as claimed in claim 1, wherein the moment force acting counter to the flexion buckling is increased as the angle of pivoting of the upper four bar linkage system with respect to the lower part increases.

3. The prosthetic knee joint as claimed in claim 1, wherein the upper four bar linkage system is mounted on a multi-link system, the multi-link system including the lower part, wherein pivot axes of the multi-link system do not coincide with the pivot axes of the upper four bar linkage system.

4. The prosthetic knee joint as claimed in claim 1, wherein the mechanical extension stop is operable between the distal and posterior joint members.

5. The prosthetic knee joint as claimed in claim 3, wherein the distal joint member is mounted on the lower part about an anterior pivot axis.

6. The prosthetic knee joint as claimed in claim 3, wherein the posterior joint member is mounted to the distal joint member at a distal pivot axis, and the posterior joint member has a portion thereof that extends beyond the distal pivot axis.

7. The prosthetic knee joint as claimed in claim 6, wherein the spring element is connected to the lower part at a distal bearing point, and is connected to the upper four bar linkage at a proximal bearing point, and a connecting line between the distal bearing point and the proximal pivot axis extends anteriorly with respect to the distal pivot axis of the posterior joint member.

8. The prosthetic knee joint as claimed in claim 1, further comprising a medial spring element operable to generate a medial spring force during swing phase flexion, the medial spring element being connected to the distal joint member at a distal bearing point and to the proximal joint member at a proximal bearing point.

9. The prosthetic knee joint claim 6, wherein the distal and proximal bearing points do not coincide with pivot axes of the four bar linkage system.

10. The prosthetic knee joint as claimed in claim 1, wherein the spring element is designed as a compressible elastomer element.

11. A prosthetic knee joint, comprising:
    a multi-member joint system comprising:
        a first joint member;
        an anterior joint member pivotably coupled to the first joint member at a proximal end of the anterior joint member;
        a posterior joint member pivotably coupled to the first joint member at a proximal end of the posterior joint member, the posterior joint member being arranged posterior to the anterior joint member;
        a distal joint member pivotably coupled to a distal end of the anterior joint member and pivotably coupled to the posterior joint member at a location between distal and proximal ends of the posterior joint member;
    a mechanical extension stop;
    a lower part pivotably coupled to the distal joint member;
    a distal fastening device coupled to the lower part and configured to connect to a distal prosthetic member;
    a proximal fastening device coupled to the first joint member and configured to connect to a proximal prosthetic member;
    a spring element pivotally connected to the lower part and to the posterior joint member, the spring element providing a spring force, the spring force having an action line oriented along a length of the spring element;
    wherein the multi-member joint system is pivotable relative to the lower part from a starting position to a rotated position counter to the spring force during a stance phase flexion, and the action line of the spring force is oriented to provide a moment force on the extension stop to fix the joint members relative to each other and counteract a flexion buckling of the multi-member joint system during stance phase flexion.

12. The prosthetic knee joint of claim 11, wherein the multi-member joint system further comprises:
an anterior pivot axis coupling the first joint member and the anterior joint member;
a posterior pivot axis coupling the first joint member and the posterior joint member;
a distal pivot axis coupling the anterior joint member and the distal joint member;
a fourth pivot axis coupling the posterior joint member and the distal joint member;
wherein distances between the pivot axis are fixed during stance phase flexion and the joint members rotate with respect to one another during swing phase flexion.

13. The prosthetic knee joint of claim 12, further comprising:
a proximal pivot axis located on the lower part, the proximal pivot axis coupling the distal joint member to the lower part;
a medial spring element pivotally connected to the first joint member at a proximal end of the medial spring element, and pivotally connected to the distal joint member at a distal end of the medial spring element.

14. The prosthetic knee joint of claim 13, wherein a medial spring element is connected to the first joint member at a location spaced between the anterior and posterior pivot axes.

15. The prosthetic knee joint of claim 13, wherein the spring element comprises an elastomer element and is positioned to hold the multi-member joint system in the starting position.

16. The prosthetic knee joint of claim 12, further comprising:
a medial spring element arranged inside the multi-member joint system, the medial spring element coupled to the first joint member and the distal joint member;
a distal bearing point located on the distal joint member between the distal pivot axis and the fourth pivot axis, the distal bearing point coupling the medial spring element to the distal joint member.

17. The prosthetic knee joint of claim 11, wherein the first joint member is substantially horizontally oriented.

18. The prosthetic knee joint of claim 11, wherein displacement of the multi-member joint system relative to the lower part enables the lower part to rotate relative to the proximal fastening device during a swing phase of the prosthetic knee joint.

* * * * *